US 8,598,876 B2

(12) United States Patent
Rapoport

(10) Patent No.: US 8,598,876 B2
(45) Date of Patent: *Dec. 3, 2013

(54) IMAGING DEVICE FOR THREE DIMENSIONAL ANATOMICAL AND FUNCTIONAL IMAGING AND METHODS THEREOF

(75) Inventor: Uri Rapoport, Moshav Ben Shemen (IL)

(73) Assignee: Aspect Imaging Ltd., Shoham (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/266,371

(22) PCT Filed: Apr. 21, 2010

(86) PCT No.: PCT/IL2010/000313
§ 371 (c)(1),
(2), (4) Date: Oct. 26, 2011

(87) PCT Pub. No.: WO2010/125559
PCT Pub. Date: Nov. 4, 2010

(65) Prior Publication Data
US 2012/0043963 A1   Feb. 23, 2012

Related U.S. Application Data

(60) Provisional application No. 61/172,784, filed on Apr. 27, 2009.

(51) Int. Cl.
*G01R 33/34007* (2006.01)
*G01R 33/4808* (2006.01)
*G01R 33/481* (2006.01)
*A61B 5/0073* (2006.01)
*A61B 5/0055* (2006.01)

(52) U.S. Cl.
USPC ........... 324/309; 324/307; 324/318; 600/425; 600/427; 600/421; 600/411

(58) Field of Classification Search
USPC .......... 324/300–322; 600/407–435, 473, 476, 600/18; 382/128–131, 134
See application file for complete search history.

(56) References Cited

U.S. PATENT DOCUMENTS 5,166,875 A    11/1992   Machida
5,713,364 A *  2/1998   DeBaryshe et al. .......... 600/476

(Continued)

FOREIGN PATENT DOCUMENTS

WO    2008028904 A1    3/2008

OTHER PUBLICATIONS

International Search Report and Written Opinion dated Sep. 1, 2010 in corresponding International Application No. PCT/IL2010/000313.

(Continued)

*Primary Examiner* — Patrick Assouad
*Assistant Examiner* — Tiffany Fetzner
(74) *Attorney, Agent, or Firm* — The Law Office of Michael E. Kondoudis

(57) ABSTRACT

The present invention discloses an imaging device within an MRI. In a magnetic resonance imaging system, a spatially fixed coupled imaging device (SFCID) for producing combined anatomical and real time functional light images, the SFCID functionally incorporates a maneuverable imaging system MIS with a coupled imaging system CIS.

14 Claims, 6 Drawing Sheets

(56) References Cited

U.S. PATENT DOCUMENTS

| | | | |
|---|---|---|---|
| 5,813,987 A * | 9/1998 | Modell et al. | 600/473 |
| 6,138,302 A | 10/2000 | Sashin et al. | |
| 6,275,722 B1 | 8/2001 | Martin et al. | |
| 6,426,623 B1 | 7/2002 | Bernstein | |
| 6,591,128 B1 | 7/2003 | Wu et al. | |
| 6,961,606 B2 | 11/2005 | DeSilets et al. | |
| 7,266,406 B2 | 9/2007 | Kroeckel | |
| 8,290,228 B2 * | 10/2012 | Cohen et al. | 382/128 |
| 2005/0054910 A1 * | 3/2005 | Tremblay et al. | 600/411 |
| 2006/0258941 A1 | 11/2006 | Cable et al. | |
| 2008/0087833 A1 | 4/2008 | McCroskey et al. | |
| 2010/0222671 A1 * | 9/2010 | Cohen et al. | 600/424 |
| 2010/0228076 A1 * | 9/2010 | Blank et al. | 600/18 |
| 2010/0290693 A1 * | 11/2010 | Cohen et al. | 382/134 |
| 2011/0142316 A1 * | 6/2011 | Wang et al. | 382/131 |
| 2011/0282181 A1 * | 11/2011 | Wang et al. | 600/407 |
| 2012/0043963 A1 * | 2/2012 | Rapoport | 324/307 |
| 2012/0065494 A1 * | 3/2012 | Gertner et al. | 600/411 |
| 2012/0165654 A1 * | 6/2012 | Rapoport | 600/411 |

OTHER PUBLICATIONS

Green et al., Head Movement in Normal Subjects During Simulated PET Brain Imaging with and without Head Restraint, The Journal of Nuclear Medicine, Sep. 1994, pp. 1538-1546, vol. 35, No. 9.

* cited by examiner

IMAGING DEVICE FOR THREE DIMENSIONAL ANATOMICAL AND FUNCTIONAL IMAGING AND METHODS THEREOF

FIELD OF THE INVENTION

This invention generally relates to a device used to image animals or humans, and methods thereof. Specifically, the invention relates to producing 3D in vivo, time resolved images from a multi-modality imaging device.

BACKGROUND OF THE INVENTION

Optical imaging, which is one modality of molecular imaging, is a new and emerging discipline that enables mapping in-vivo functions using bio-markers. The bio-markers, introduced into a human or an animal, emits light, either spontaneously or in response to stimulation, which is received by specialized detectors. Since the detectors can gather continuous data, they supply functional information over time. However, a single detector can only supply a two dimensional image, and to determine the 3D location of the process which has taken place, a co-registration, or image fusion, is required. Additionally, since the radiation detected by optical imaging results from diffusive radiation (as opposed to ballistic radiation encountered, for example, in X-rays), it is difficult to reconstruct an image. Therefore, for identifying the location of a desired function, another modality, providing anatomical correlation, such as CT or MRI, is required. The image from the additional modality is then integrated or fused with the data from the optical imager, to form a 3D data set. Furthermore, each modality has its limiting characteristics: an optical imager requires a space which is as sealed to light as possible. An MRI requires an environment which shields it from external magnetic fields, and restricts the use of paramagnetic objects in its vicinity. The surroundings of a CT or nuclear medicine machine have to be shielded from ionizing radiation. Nuclear medicine imaging devices also have to be close to a radiation source.

Prior art shows, that in order to use optical imaging in addition to another modality, the imaged subject is extracted from the optical imager and transferred to another device. For example, US patent application 2006/0258941 to Cable et al, teaches of a subject handling system, comprising a track and a robotic manipulator, which automatically moves the subject between the optical imager and a second imaging system, mainly an MRI.

Other companies providing optical imaging devices offer special containers, in which the subject rests, usually anesthetized. The containers are manually relocated from one modality to the other.

The above solutions require that the subject will be completely immobile between procedures, and that the imaging facilities will be close. However, even under best conditions, the subject might be slightly rotated, or not be properly centered in the imaging device, or even just breathe, which results in anatomical deviation of monitored functions.

Patent application US 2008/0087833 discloses a multi-modality detection system for imaging a region of interest, including a patient organ such as the breast or brain. The region of interest is scanned with a gamma detector and an x-ray detector rotating on a rotatable table, producing SPECT and "micro CT" images. The setting is, however, not compatible for MR imaging because gamma-rays cannot be rotated inside the bore of the magnet, and the electronic components of the machine are harmed by the ionizing radiation. The system disclosed is also not compatible with optical imaging, which requires a setting which is sealed to light. Several disclosures have been made of devices that enable partial or total removal of a receiver coil from within the MRI while the patient remains inside it. For example. U.S. Pat. No. 6,591,128 to Wu et al. discloses an RF coil system with a detachable, relocatable, or interchangeable section. This invention was designed to provide a solution to a different problem with using a separate receiver coil, namely, that its presence within the already-crowded space within the MRI device limits the amount and type of additional instrumentation that can be included in the system. The RF coil system disclosed in the invention of Wu et al. was designed particularly for use in brain imaging, specifically, to allow accommodation of medical devices such as tubes and other therapeutic or life support devices and accommodation for instruments such as probes for functional MRI studies.

U.S. Pat. No. 7,266,406 to Kroeckel discloses another approach to construction of an MRI instrument with a movable receiver coil. This invention discloses an apparatus in which the distance from the receiver coil to the patient's body can be altered via translation of the coil towards or away from the patient's body. The goal of this invention was to provide the increased accuracy of close contact between the receiver coil and the volume probed with the ability to accommodate additional instruments, as well as to reassure the patient by limiting the amount of time spent in the fully constricted space created by the aforementioned close contact between the receiver coil and the patient's body. This invention does not provide any means for moving the receiver coil parallel to the main field axis (i.e. parallel to the plane on which the subject lies during acquisition of the MRI information). Rather, it provides for a plurality of receiver coils positioned along the axis, with the subject physically moved to a particular receiver coil. Of course, having multiple receiver coils adds to the expense and complexity of the MRI system.

A third example of an MRI system with a movable receiver coil is found in U.S. Pat. No. 6,275,722 to Martin et al., which discloses an MRI system with an RF receiver coil that can be swept over the region of interest. The receiver coil in this invention is designed to be swept through a volume of interest within the body of a patient, primarily in order to enable a surgeon to determine whether an operation (e.g. tumor excision) has been successful by enabling accurate MRI of the small volume of tissue in which the operation was performed.

All of these designs suffer from an additional disadvantage that while the best spatial resolution can be obtained when the volume being proved by the receiver coil is located at the midpoint of the MRI's static magnetic field, none of the designs disclosed in the above patents has the ability to place simultaneously the volume being investigated and the receiver coil at that point.

U.S. Pat. No. 6,961,606 to DeSilets et al. discloses a multimodality medical imaging system in which a plurality of tomographic imaging scanners can be used on a single patient. In this apparatus, the patient is translated through the different scanners sequentially. While this device does enable the use of a detached receiver coil for MRI along with any other probe technique desired, it suffers from a different disadvantage. Since the patient is physically moved from one point to another, matching the images produced by the different scanners must be done subsequently, and the matching accuracy necessarily suffers. For example, it may not be possible to determine with certainty whether a feature in an MRI image originates from the same point as a feature in a second image, especially if the size of the feature is small or the signal arising from it is weak.

Pursuant to the prior art, there is therefore a long felt and unmet need for an imaging device and method providing accurate three dimensional images of internal subjects and bodily tissues over time. Furthermore, there is a long felt and unmet need for an imaging device and method accurately providing three dimensional images of internal subjects and bodily tissues over time, the three dimensional images being comprised of NMR derived images and optically derived images. Moreover, there is a long felt and unmet need for an imaging device and method accurately providing three dimensional images of an internal bodily process over time. Lastly, there is a long felt and unmet need for an imaging device and method accurately providing three dimensional images of an internal pathological bodily process over time.

SUMMARY OF THE INVENTION

The present invention discloses, in a magnetic resonance imaging system, a novel spatially fixed coupled imaging device (SFCID) useful for producing combined anatomical and real time functional light images. The SFCID functionally incorporates a maneuverable imaging system MIS with a coupled imaging system CIS. The maneuverable imaging system (MIS) contains, inter alia, an imaging platform (IMP) accommodating an immobilized subject positioned within a nonconductive housing. The IMP is contained within a radio frequency coil system (RFCS) for imaging one or more regions of a subject. The RFCS is adapted either to reversibly translate (i) at least one conductive receiver coil, and/or (ii) at least a portion of the IMP, in at least one nonconductive housing coil to at least one fixed position to an accuracy of not less than about 3 mm, while the subject remains within the MIS. The RFCS includes, inter alia, a mechanical translation system (MTS) adapted for providing linear motion to the immobilized subject and for reproducibly fixing the position of the immobilized subject to within a range of about 3 to about 60 mm. The RFCS also includes attaching means (AM) for connecting the housing to the MTS. The coupled imaging system (CIS) is adapted to image at least one specific region of the immobilized subject, and to integrate (i) at least one MRD imaging module (MIM) configured for providing three dimensional anatomical images; with (ii) at least one optical imaging module (OIM), coupled to the IMP and configured for detecting photons emitted or reflected by the region of the immobilized subject so as to generate real time functional light images of a functionally active part of the region of the immobilized subject. Thus, the functional incorporation of coupled MIM and OIM in the IMP provides one or more multi-modular fused, real-time images of the region of the immobilized subject located within a determinable specific volume.

It is also in the scope of the invention wherein the aforesaid RF coil is selected from the group consisting of a solenoid, a Helmholtz coil, and a surface coil.

It is also in the scope of the invention wherein the magnetic resonance imaging system defined above further comprises one or more of the following modules: (a) a nonconductive housing which defines a volume of interest (VOI); (b) a magnet adapted for generating a stable magnetic field with a defined magnetic field axis in the VOI; (c) a plurality of coils adapted for establishing at least one magnetic gradient within the VOI; (d) at least one non-conductive housing coil (NCHC) adapted for applying pulses of RF radiation to excite nuclear spins within the immobilized subject in the VOI; and, (e) at least one conductive receiver coil (CRC) located within the NCHC. The CRC is adapted to optimize reception of resonance signals emanating from the immobilized subject within a determinable specific volume provided within the VOI.

It is also in the scope of the invention wherein at least one of the fixed positions is located outside of the nonconductive housing.

It is also in the scope of the invention wherein one of the fixed positions is the point at which the optimized reception occurs at the point along the midpoint of the stable magnetic field along the magnetic field axis.

It is also in the scope of the invention wherein at least one of the fixed positions is located outside of the volume and one of the fixed positions is the point at which the optimized reception occurs at the point along the midpoint of the stable magnetic field along the magnetic field axis.

It is also in the scope of the invention wherein the imaging platform (IMP) is a bad, operation table, hammock-like furniture, stretcher or the like.

It is also in the scope of the invention wherein the magnetic resonance imaging system as defined in any of the above further comprises (a) a second mechanical translation system (MTS) adapted for providing linear motion to the immobilized subject and for reproducibly fixing the position of the immobilized subject within a range of about 3 mm to about 60 mm; and, (b) attaching means (AM) for connecting the IMP or portions thereof to the MTS; wherein the IMP is adapted reversibly to translate relative to the determinable specific volume independent of the translation of the CRC.

It is also in the scope of the invention wherein the AM is adapted to connect the mechanical translation system (MTS) attached to the IMP with the MTS attached to the CRC, and/or wherein the motions of the IMP and CRC are interdependent.

It is also in the scope of the invention wherein the optical imaging module (OIM) inter alia comprises (a) a plurality of detectors functionally incorporated within the perimeter of the housing; and, (b) means for transmitting a signal from each of the plurality of detectors to a controller located external to the volume. The functional incorporation of the plurality of detectors within the hosing enables production combined anatomical and real time functional light images.

It is additionally or alternatively in the scope of the invention wherein the optical imaging module (OIM) inter alia comprises (a) a plurality of optic fibers functionally incorporated within the perimeter of the housing; and, (b) means for transmitting a signal from each of the plurality of optic fibers to a controller located external to the volume. The functional incorporation of the plurality of optic fibers within the hosing enables production combined anatomical and real time functional light images.

It is also in the scope of the invention wherein the coupled imaging system (CIS) provides an imaging method selected from the group consisting of (a) fluorescence spectroscopy, (b) SPECT, (c) PET, and any combination of the above. The plurality of either detectors and/or optics fibers is preferably adapted for detecting signals typical of the at least one additional imaging method.

It is also in the scope of the invention wherein the spatially fixed coupled imaging device (SFCID) is adapted for 3-dimensional (3D) multimodal imaging.

It is also in the scope of the invention wherein the device as defined in any of the above is provided with a self-fastening cage of a magnetic resonance device (MRD) for providing a homogeneous, stable and uniform magnetic field therein, characterized by an outside shell comprising at least three flexi-jointed superimposed walls disposed in a predetermined arrangement clockwise or counterclockwise.

It is also in the scope of the invention wherein the self-fastening cage of an MRD inter alia comprises: (a) at least six side-magnets arranged in two equal groups being in a face-to-face orientation in a magnetic connection with the cage walls characterized by an outside shell comprising at least three flexi-jointed superimposed walls disposed in the same predetermined arrangement of the cage walls, increasing the overall strength of the magnetic field provided in the cage; (b) at least two pole-magnet pieces, arranged in a face-to-face orientation in between the side-magnets; and, (c) at least two main-magnets, located on the pole-pieces, arranged in a face-to-face orientation, generating the static magnetic field therein the cage. It is still in the scope of the present invention wherein the self-fastening cage's contour is defined in a by a polyhedron such that tetrahedron, pentahedron or hexahedron. It is still in the scope of the present invention wherein the superimposed walls and pole-pieces are metal alloys, preferably a soft iron alloy. It is still in the scope of the present invention wherein at least one of the cage walls is interconnected with adjacent wall by means of a protruding-edge connection defining a tolerance enabling the cage's wall to displace, and to prevent leakage of the cage's magnetic field. It is still in the scope of the present invention wherein at least a portion of side-magnets are superconductors or ferromagnets. It is still in the scope of the present invention wherein the pole-pieces are separated by an air gap at a predetermined distance (F). It is still in the scope of the present invention wherein the pole-piece area, the dimensions of side-magnets, i.e. its thickness (C), width (D), length (E), the main magnet and the air gap (F) determine the magnetic field strength and its uniformity. It is still in the scope of the present invention wherein the self-fastening cage further comprising at least one corner-magnet adapted to adjust the magnetic field therein. It is still in the scope of the present invention wherein the corner-magnets form a polyhedron, cylinder or any combination thereof. It is still in the scope of the present invention wherein at least one cylinder corner-magnet comprises at least one bore exceeded along the corner magnet's longitudinal axis, adapted thus to accommodate a rotating means suitable for adjusting the magnetic field provided in the cage. It is still in the scope of the present invention wherein at least one cylinder corner-magnet is rotated clockwise or counterclockwise. It is also in the scope of the present invention wherein the corner-magnets are positioned at a predetermined location adjacent to the corner of the cage, so that a pre-adjustment of the magnetic field is provided. The corner-magnets are placed outside the pole-pieces, inside the pole-pieces, between the side magnets, at any distance from the pole-pieces and from the side magnets, or any combination thereof. It is further in the scope of the present invention, wherein the corner-magnet is defined by parameters; namely the angle between the flux line of the magnet and the edge of the pole-piece ([alpha]), its length (A) and its width (B).

It is also in the scope of the present invention wherein a method is provided for obtaining a self-fastening cage as defined in any of the above, characterized by an outside shell, comprises inter alia steps of superimposing at least three flexi-jointed walls so that a homogeneous, stable and uniform magnetic field is provided therein. The method may additionally comprise steps of constructing a self-fastening cage and a cavity encapsulate therein; and superposing corner-magnets enabling a homogeneous, stable and uniform magnetic field therein. The said method may comprise steps of adjusting [alpha] to optimize the uniformity of the field. [The method may comprise steps of rotating one or more cylinder corner-magnets hence providing fine adjustments of the magnetic field; directing the flux line; and compensating the field created by impurities occurred during the manufacturing process of magnet materials.

It is also in the scope of the invention wherein the device as defined in any of the above comprises, inter alia, at least one Central Processing Unit (CPU) for processing and integrating the three dimensional MRD images received from the at least one MRD imaging module (MIM) and the real time functional light images received from the at least one optical imaging module (OIM). The CPU is possibly provided with means to display the three dimensional MRD images and the real time light images. The CPU is alternatively or additionally provided with means for distinguishing the real time light images from the three dimensional NMR images of the region of the immobilized subject such that functionally active parts of the region of the immobilized subject are identifiable in real time.

It is also in the scope of the invention wherein the MRD module of the device as defined in any of the above comprises CT analyzing means and/or MRI analyzing means.

It is also in the scope of the invention wherein the MRD module of the device as defined in any of the above is provided with Two-Dimensional Fourier Transform (2DFT) means and slice selection means for building at least a portion of the image, and/or with Three-Dimensional Fourier Transform (3DFT) means for building at least a portion of the image.

It is also in the scope of the invention wherein the MRD module of the device as defined in any of the above is provided with projection reconstruction means for building the image.

It is also in the scope of the invention wherein the MRD module of the device as defined in any of the above is provided with a point by point image building means for building the image.

It is also in the scope of the invention wherein the MRD module of the device as defined in any of the above is provided with a line by line image building means for building the image.

It is also in the scope of the invention wherein the MRD module of the device as defined in any of the above is provided with a static field gradient image building means for building the image.

It is also in the scope of the invention wherein the MRD module of the device as defined in any of the above is provided with an RF field gradient image building means for building the image.

It is also in the scope of the invention wherein the optical imaging module as defined in any of the above comprises a light detector array including a plurality of light detectors distributed around the imaging platform in a predetermined manner for providing, three dimensional real time light images of the region the immobilized subject.

It is also in the scope of the invention wherein the optical imaging module as defined in any of the above is provided with means for detecting bioluminescence of the region of the immobilized subject.

It is also in the scope of the invention wherein the optical imaging module as defined in any of the above is provided with means for detecting chemiluminescence of the region of the immobilized subject.

It is also in the scope of the invention wherein the optical imaging module as defined in any of the above is provided means for detecting fluorescence of the region of the immobilized subject.

It is also in the scope of the invention wherein the optical imaging module as defined in any of the above is provided with means for detecting near infra-red fluorescence of the region of the immobilized subject.

It is also in the scope of the invention wherein the optical imaging module as defined in any of the above is provided for single photon emission computed tomographic imaging (SPECT) of the region the immobilized subject.

It is also in the scope of the invention wherein the optical imaging module as defined in any of the above includes means for Positron Emission Tomographic imaging (PET) of the region of the immobilized subject.

The magnetic resonance imaging system of claim 1, wherein the optical imaging module includes photon counting sensitivity means.

It is also in the scope of the invention wherein the optical imaging module as defined in any of the above includes means for selectively detecting excitation pulses traveling back from the region of the immobilized subject.

It is also in the scope of the invention wherein the optical imaging module as defined in any of the above includes means for synchronizing the excitation pulses.

It is also in the scope of the invention wherein the immobilized subject defined in any of the above is a small mammal. Preferably, yet not exclusively the immobilized subject is selected from a group consisting of humans, mammals, biological specimens, biological organs, mice, rats, rodents, birds, reptiles, amphibians, in vivo biological tissue or organ or ex vivo biological tissue or organ.

It is also in the scope of the invention to disclose a method for producing combined anatomical and real time functional light images, by functionally incorporating a maneuverable imaging system MIS with a coupled imaging system CIS. The method comprises, inter alia, one or more of the following steps: (a) providing a spatially fixed coupled imaging device (SFCID) in a magnetic resonance imaging system, providing the MIS with an imaging platform (IMP) accommodating an immobilized subject positioned within a nonconductive housing; (b) providing the IMP within a radio frequency coil system (RFCS) for imaging one or more regions of a subject; (c) providing the RFCS with means to either reversibly translate (i) at least one conductive receiver coil (CRC), and/or (ii) at least a portion of the IMP, in at least one nonconductive housing coil (NCHC) to at least one fixed position to an accuracy of not less than about 3 mm while the subject remains within the MIS; (d) further providing the RFCS with a mechanical translation system (MTS), and attaching means (AM) for connecting the housing to the MTS by means of the MTS, maneuvering the immobilized subject in a linear motion, and reproducibly fixing the position of the immobilized subject to within a range of about 3 to about 60 mm; (e) imaging at least one specific region of the immobilized subject, by integrating (i) at least one MRD imaging module (MIM) configured for providing three dimensional anatomical images; with (ii) at least one optical imaging module (OIM), coupled to the IMP and configured for detecting photons emitted or reflected by the region of the immobilized subject thus generating real time functional light images of a functionally active part of the region of the immobilized subject; and, (f) functionally incorporating MIM and OIM in the IMP, thus providing one or more multi-modular fused, real-time images of the region of the immobilized subject located within a determinable specific volume.

It is also in the scope of the invention wherein the method comprises steps of (a) introducing the immobilized subject to a determinable specific position within a stable magnetic field generated by a magnet; (b) placing a positionable NCHC in proximity to the immobilized subject such that the position of the NCHC is fixed to within about 3 mm to about 60 mm and such that at least part of the volume of interest is located within the volume defined by the NCHC; (c) exciting nuclear magnetization in the volume of interest by applying RF pulses and magnetic field gradients according to a predetermined imaging protocol; (d) receiving RF imaging signals generated in the NCHC by the excited nuclear magnetization; and, (e) reconstructing a magnetic resonance image of the determinable specific volume from the received magnetic resonance imaging signals and from the position of the NCHC.

It is also in the scope of the invention wherein a method for optimizing reception of resonance signals emanating from the determinable specific volume is provided as defined above, wherein the step of placing an NCHC in proximity to the object further includes a step of placing the NCHC at the point along the midpoint of the stable magnetic field along the magnetic field axis.

It is also in the scope of the invention to disclose a method as defined above, wherein the method comprises, inter alia, steps of (a) introducing the immobilized subject to a determinable specific position, the position located within a volume at least part of the interior of which contains stable magnetic field generated by a magnet and about the perimeter of which a plurality of detectors are disposed; (b) placing a positionable RF receiver coil in proximity to the object such that the position of the RF receiver coil is fixed to within X mm and such that at least part of the volume of interest is located within the volume defined by the coil; (c) exciting nuclear magnetization in the volume of interest by applying RF pulses and magnetic field gradients according to a predetermined imaging protocol; (d) receiving RF imaging signals generated in the RF receiver coil by the excited nuclear magnetization; (e) reconstructing a magnetic resonance image of the volume of interest from the received magnetic resonance imaging signals and from the position of the RF receiver coil; and, (f) transmitting a signal from each of at least one of the plurality of detectors to a controller located external to the volume, the transmission commencing at a predetermined time relative to the commencement of step (c) and continuing for a predetermined length of time. X is any integer number, e.g., X is ranging between about 0.1 mm to about 50 mm; between about 5 mm to about 500 mm, between about 50 mm to 1.5 m etc.

It is also in the scope of the invention wherein a method is provided as defined above, and at least one other imaging technique is selected from the group consisting of (a) fluorescence spectroscopy; (b) SPECT; (c) PET; and (d) any combination thereof.

BRIEF DESCRIPTION OF FIGURES

In order to understand the invention and to see how it may be implemented in practice, a few preferred embodiments will now be described, by way of non-limiting example only, with reference to the accompanying drawings, in which.

DETAILED DESCRIPTION OF THE DRAWINGS

Figure 1:
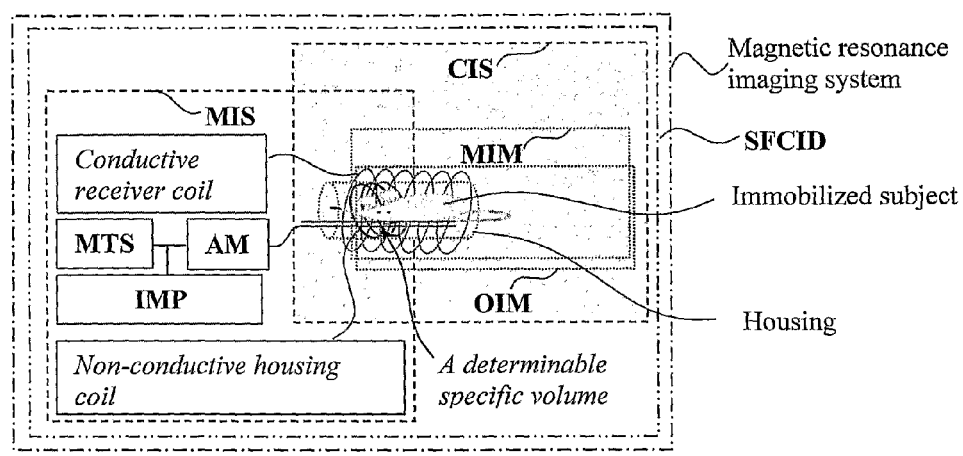
FIG. 1 presents a schematic diagram of a novel spatially fixed coupled imaging device (SFCID) useful for producing combined anatomical and real time functional light images. The SFCID functionally incorporates a maneuverable imaging system MIS with a coupled imaging system CIS according to an embodiment of the invention herein disclosed.

The following description is provided, alongside all chapters of the present invention, so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide means and method of producing in vivo, time resolved, images, from a multi-modality imaging device.

It should also be appreciated that the above described description of methods and apparatus are to be interpreted as including apparatus for carrying out the methods, and methods of using the apparatus of any type as well known to a person or ordinary skill, and which need not be described in detail herein for enabling a person of ordinary skill to practice the invention.

The term 'magnetic resonance device' (MRD) applies hereinafter to any Magnetic Resonance Imaging (MRI) device, any Nuclear Magnetic Resonance (NMR) spectroscope, any Electron Spin Resonance (ESR) spectroscope, any Nuclear Quadruple Resonance (NQR) or any combination thereof.

The terms "modality, modalities, mode" refers herein in a non limiting manner to an attribute of the device of the invention which is that the device is provided with more than one means for generating an image or images. In preferred embodiments, the device is provided with NMR means or modalities to generate images of a subject, such as MRI or CT, and also, the very same device is provided with optical means or modalities for generating images of the same subject. Both NMR means and optical means may generate time resolved images.

The term "anatomical imaging" refers hereinafter in a non-limiting manner to NMR based imaging techniques, methods, means and equipment which are used for reconstructing anatomical images, such as Computed Tomography (CT) or Magnetic Resonance (MR) imagers.

The term "functional imaging" refers hereinafter in a non-limiting manner to an optical imaging techniques, methods, means and equipment for detecting or measuring changes in function of an organism, tissue, organ or body part or portion. The functions are, in a non limiting manner, metabolism, blood flow, regional chemical composition, and absorption, as well as any other modality used for molecular imaging. Such functions may be detected by optical detectors or sensors adapted for any technique, method or means selected from a group consisting, of optical imaging, optical fluorescence imaging, molecular imaging, bioluminescence, chemiluminescence, fluorescence, UV, IR and/or visible light, Single photon emission computed tomography (SPECT) and Positron emission tomography (PET).

As used herein, the term "subject" refers to any object or living creature inserted in whole or in part into the static magnetic field of a magnetic resonance imaging (MRI) system in order to obtain at least one magnetic resonance image thereof or therefrom.

As used herein, the term "volume of interest" refers to a volume within the subject of which an image is desired. The volume of interest thus may be, for example, the entire subject, an organ within the subject, or a specific volume within an organ within the subject (e.g. the site at which a tumor is suspected to exist).

As used herein, the term "bed" refers to any object, upon a surface of which the subject rests during acquisition of magnetic resonance images by an MRI system. As a non-limiting example, the surface on which the subject rests is the upper surface of the object and is essentially planar. The bed may be translatable to a position located external to the MRI.

As used herein, the term "coil" refers to any generally circular or spiral electrically conducting component, particularly one adapted for use in the transmission or reception of radio-frequency (RF) radiation.

As used herein, the term "midpoint" refers, with reference to a magnetic field, to the point along the magnetic field axis equidistant from two planes perpendicular to the magnetic field axis that together define two limits of a predefined volume.

As used herein, the term "detector" refers to an apparatus adapted for measuring the intensity of a signal impinging upon it and transmitting that intensity to a recording device. The detector will in general include all of the necessary electronics (and, in the case where the signal is made up of photons, optics) to convert the received signal to a current, voltage, or number proportional to the intensity of the signal and means for passing the current, voltage, or number to an appropriate recording device.

As used herein, the term "plurality" refers in a non-limiting manner to any integer equal or greater than 1.

The term 'about' applies hereinafter to a measure being ±25% of the defined value.

Reference is now made to FIG. 1, schematically illustrating in a non-limited manner a block diagram of a magnetic resonance imaging system according to one embodiment of the invention. The magnetic resonance imaging system comprises a novel spatially fixed coupled imaging device (SF-CID) useful for producing combined anatomical and real time functional light images. The SFCID functionally incorporates a maneuverable imaging system MIS with a coupled imaging system CIS. The maneuverable imaging system (MIS) contains, inter alia, an imaging platform (IMP) accommodating an immobilized subject positioned within a non-conductive housing. The IMP is contained within a radio frequency coil system (RFCS) for imaging one or more regions of a subject. The RFCS is adapted either to reversibly translate (i) at least one conductive receiver coil, and/or (ii) at least a portion of the IMP, in at least one nonconductive housing coil to at least one fixed position to an accuracy of not less than about 3 mm, while the subject remains within the MIS. The RFCS includes, inter alia, a mechanical translation system (MTS) adapted for providing linear motion to the immobilized subject and for reproducibly fixing the position of the immobilized subject to within a range of about 3 to about 60 mm. The RFCS also includes attaching means (AM) for connecting the housing to the MTS. The coupled imaging system (CIS) is adapted to image at least one specific region of the immobilized subject, and to integrate (i) at least one MRD imaging module (MIM) configured for providing three dimensional anatomical images; with (ii) at least one optical imaging module (OIM), coupled to the IMP and configured for detecting photons emitted or reflected by the region of the immobilized subject so as to generate real time functional light images of a functionally active part of the region of the immobilized subject. Thus, the functional incorporation of coupled MIM and OIM in the IMP provides one or more multi-modular fused, real-time images of the region of the immobilized subject located within a determinable specific volume.

Figure 2:
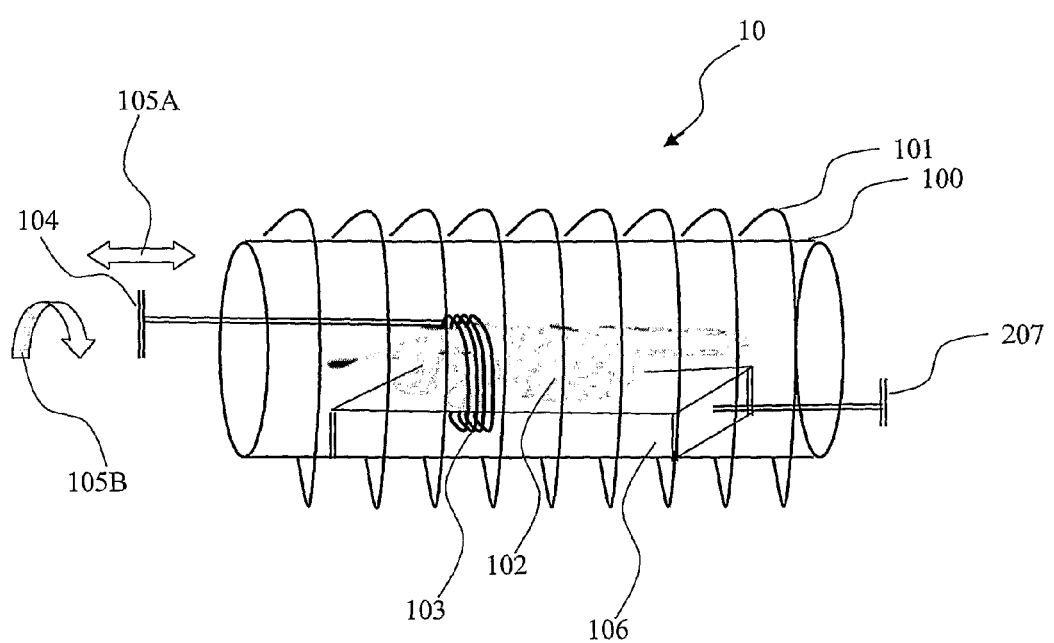
FIG. 2 presents a schematic diagram of an MRI system incorporating a positionable MRI receiver coil assembly according to an embodiment of the invention herein disclosed.

Reference is now made to FIG. 2, which presents a schematic drawing (side view) of an SFCID 10 according to yet another embodiment of the invention, that includes the receiver coil assembly disclosed in the present invention. A static magnetic field is created by a magnet (not shown) external to MRI chamber 100. The magnet may be a superconducting magnet or a permanent magnet of any appropriate geometrical design. Also not shown in FIG. 2 are gradient coils that produce appropriate gradient magnetic fields. The design and construction of such magnets and coils is well-known in the art. A transmit coil 101, located external to MRI chamber 100, provides RF pulses to excite magnetic nuclei within the static magnetic field according to principles well-known in the art. Subject 102 (here e.g., a mouse) is positioned within chamber 100 such that the volume of interest is located within the static magnetic field and within the volume enclosed by transmit coil 101; in another embodiment, subject 102 is a human being, and the MRI instrument is adapted to obtain images of the whole body. In alternative embodiments, only a part of the subject's body (e.g. the head or a limb) is located within chamber 100; in further alternative embodiments, the subject is not a human being (as a non-limiting example, the subject can be a small mammal such as a rat or rabbit; in general; in these embodiments, the entire animal is located within the chamber). In the embodiment shown, subject 102 lies on bed 106 or similar furniture. It is yet in the scope of the invention wherein (i) both coils 101 and 103 are within the internal portion of housing 100, or (ii) wherein, as shown, coil 101 located externally to the housing and coil 103 located internally, within the housing.

Receiver coil 103 substantially encircles the volume of interest, and thus may be designed, for example, to encircle the entire body of the subject, or a limb or body part thereof, depending on the specific location within the subject of the volume of interest. Receiver coil 103 is positioned so it is as close as possible to the volume of interest. The receiver coil may be any type of RF coil, e.g. a solenoid, a Helmholtz coil, or a surface coil (loop). The inner coil does not have to be homogeneous. In the embodiment shown in FIG. 1, there is a single receiver coil; in alternative embodiments, a plurality of independent coils is present. Receiver coil is attached to mechanical translation device 104.

The mechanical translation device is adapted to move the receive coil to any predetermined position along the axis defined by the static magnetic field and in rotation around the axis (see arrows 105A and 105B, respectively). The mechanical translation device can use any appropriate means known in the art for moving the receiver coil that is also adapted for fixing its position to within X mm (e.g. via a stepper motor); X is any integer number, e.g., X is ranging between about 0.1 mm to about 50 mm; between about 5 mm to about 500 mm, between about 50 mm to 1.5 m etc. Once the receiver coil is properly positioned, MRI can proceed according to any appropriate pulse/detection scheme.

Figure 3:
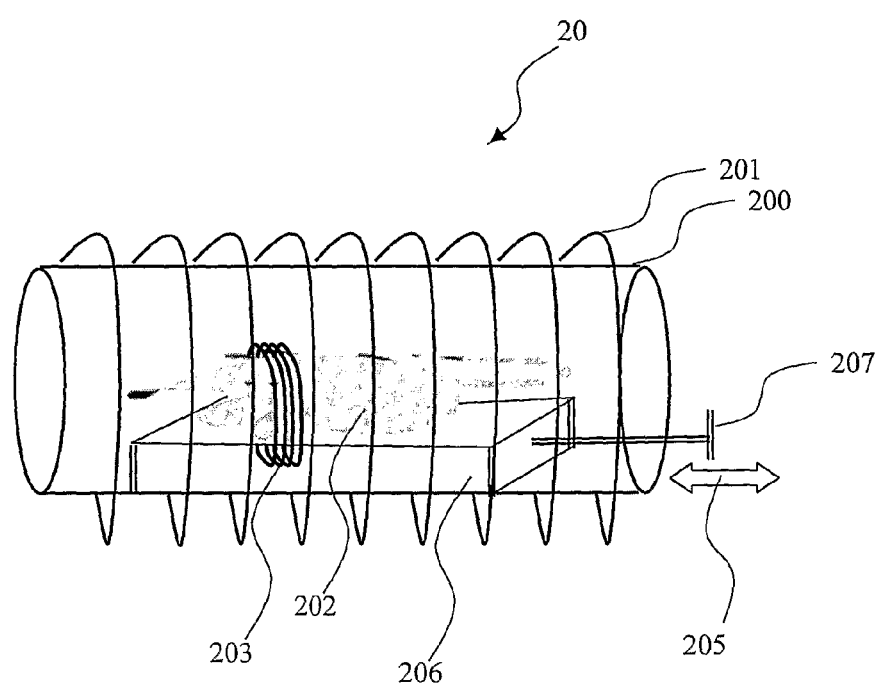
FIG. 3 presents a schematic diagram of an MRI system incorporating a positionable MRI receiver coil and independently movable bed according to an embodiment of the invention herein disclosed.

Reference is now made to FIG. 3, which illustrates schematically a side view of another embodiment 20 of the SFCID herein disclosed. This embodiment comprises all of the features of the previous embodiment: an MRI-fitted chamber 200 into which subject 202 or a portion thereof is introduced; a transmit coil 201 adapted to produce pulses of RF radiation; at least one receiver coil 203 that substantially encircles the volume of interest; means 204 for moving the receiver coil or coils in the direction of arrows 205 (i.e. parallel to the magnetic field axis of the static magnetic field); and a bed 206 upon which the subject is placed. As with the previous embodiment, the magnet that produces a static magnetic field, the gradient coils that produce magnetic field gradients, the associated electronics and controllers, all of which are well-known in the art, are not shown. This embodiment contains in addition mechanical means 207 for translating bed 206 along the direction indicated by arrows 205. This mechanical means may be any means known in the art for moving the bed to a desired location. The motion of the bed may be independent of mechanical means 204 that are used to translate receiver coil 203, or the two mechanical translation devices may be coupled so that, as non-limiting examples, the bed and the receiver coil move in tandem; they may be coupled to move in opposite directions; or they may be coupled so that motion of one is set to a predetermined fraction of the other (e.g. moving the bed through a distance D moves the coil through a distance 0.1D in a predetermined direction relative to the direction of motion of the bed). In this embodiment, it is possible to move the subject so that the volume of interest is located at the midpoint of the static magnetic field and then to scan the receiver coil over the subject such that the volume of interest is imaged. This embodiment also enables fixing the receiver coil at the midpoint of the static magnetic field and moving the subject through the coil at a predetermined velocity so that the volume of interest is scanned with the coil remaining stationary at the point at which its spatial resolution is highest.

Figure 4A:
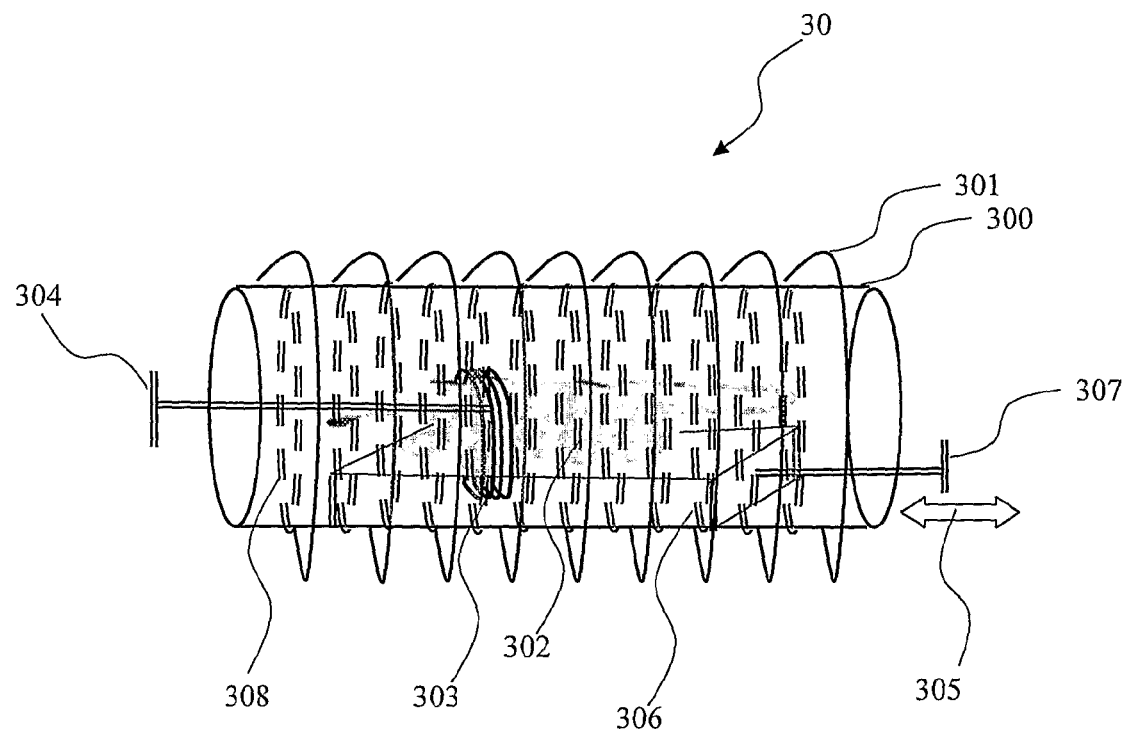
FIGS. 4a and 4b present a schematic diagram (side view and front view, respectively) of an MRI system incorporating a positionable MRI receiver coil and means for a second imaging method according to an embodiment of the invention herein disclosed.

Reference is now made to FIG. 4, showing schematically a side view of a third embodiment 30 of the SFCID herein disclosed. In addition to the elements recited in the previous embodiment (components 300-307 of embodiment 30 are exactly analogous to components 200-207 of embodiment 20), this embodiment contains a plurality of N detectors 308 disposed about the circumference of chamber 300; N is any integer number, e.g. and in a non-limiting manner, N ranges between about 1 to about 20, between about 3 to about 300 or between about 30 to about 3000. The general disposition of these detectors is shown in FIG. 4a; in various embodiments, the detectors may be disposed along the entire length of the chamber, or only along a predetermined fraction of the length of the chamber, according to the needs of the particular imaging data needed. It is in the scope of the invention wherein detectors 308 are selected, in a non-limiting manner, from a group consisting of bioluminescence, chemiluminescence, fluorescence, UV, IR and/or visible light and any combination hereof. According to the specific embodiment of the present invention, spatial location of the optical detectors is provided, and hence, triangulation of the imaged data is possible.

Figure 4B:
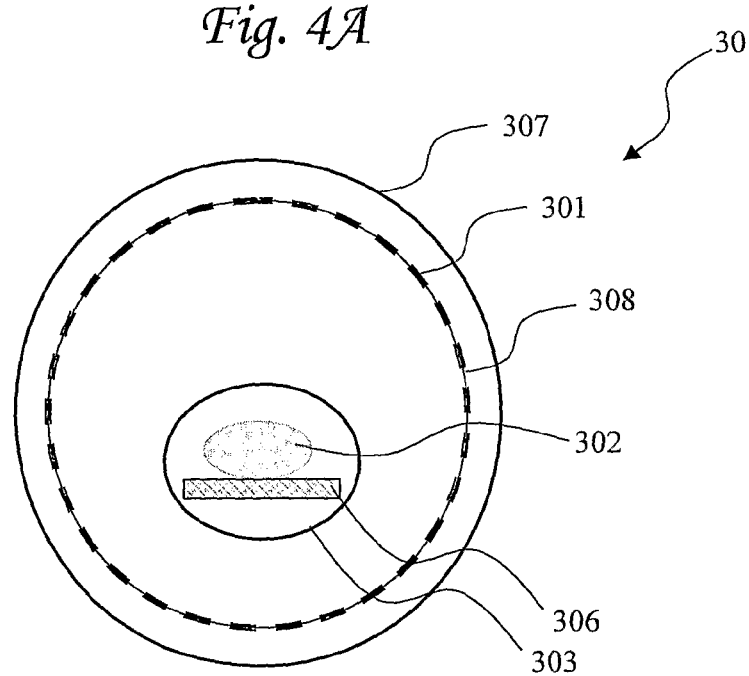

A cross-sectional slice (front or rear view) of a typical embodiment is shown schematically in FIG. 4b; in this embodiment, the detectors are disposed within the wall of the chamber. In alternative embodiments, the detectors may be attached to the inside of the chamber either in addition to or in place of detectors disposed within the wall of the chamber.

The detectors are adapted for at least one additional kind of imaging in addition to MRI; non-limiting examples include SPECT, PET, and fluorescence. The detectors are connected by any appropriate means as known in the art to a recording device (e.g., in the case of fluorescence, the detectors may be connected via appropriate fiber-optic cables to a CCD/computer assembly) such that the signal measured by each detector is separately recorded and stored. In this embodiment, the plurality of detectors enables collection and calculation of truly 3-dimensional (3D) information. In addition, the presence of the mechanical translation means 304 and 307 for moving the coil and/or bed enables direct line-of-sight access from the subject to the detectors during the collection of the image by the additional imaging means, i.e., the receiver coil is moved out of the way during the collection of the subsequent image or images without moving the subject from its position during the collection of the MRI data.

According to the embodiments defined and illustrated above, and since the subject remains stationary during the entire data collection procedure, superposition of the images obtained by MRI and by the additional method or methods is straightforward, and enables true 3-dimensional imaging of the subject.

It is thus according to yet another embodiment of the invention, wherein the functional imager disclosed in the present invention is an optical imaging modality, and the detector is an optical detector. For multi dimensional imaging, usually a plurality of detectors is required. The detectors can transform the acquired data either by optic fibers, compatible with the imaging modalities used, or by any other means of transforming information. The subject handling system can also serve to adjust the desired location of the subject in relation to the imaging device and/or strap the subject to avoid movement during the acquisition process. The device can additionally further comprise sensors to regulate the subjects or the environments conditions inside the multimodality imaging device.

Figure 5:
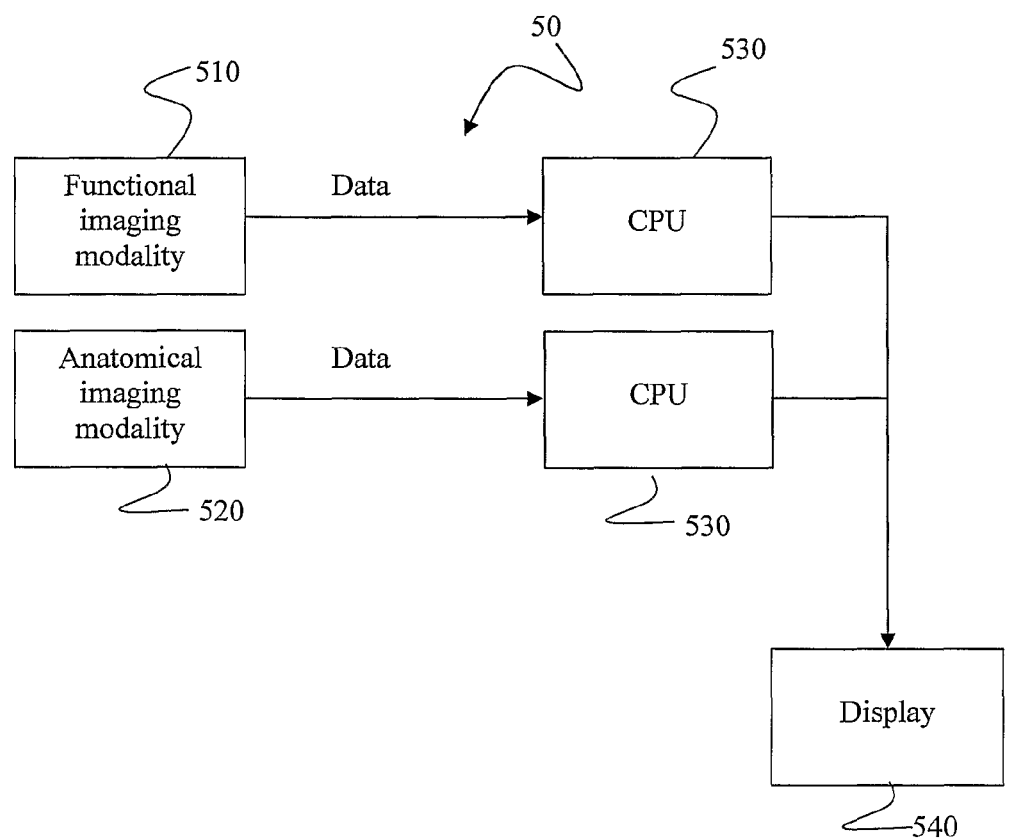
FIG. 5 presents a schematic diagram of an integrated functional imaging modality and anatomical imaging modality according to an embodiment of the invention herein disclosed.

According to yet another embodiment of the invention, as set forth in a schematic manner in block diagram of FIG. 5, a multimodality imaging system is disclosed. The system (50) comprises of a functional imager (510) and an anatomical imaging modality (520), which transform data into processors (see e.g., CPUs 530). Since the location of the subject remains the same during both scans, the reconstructed images can be fused into a single image, displaying the correlation between function and anatomy. The fused image can then be saved or displayed by means of displayer 540 in any required form (either hard copy or soft copy).

Figure 6:
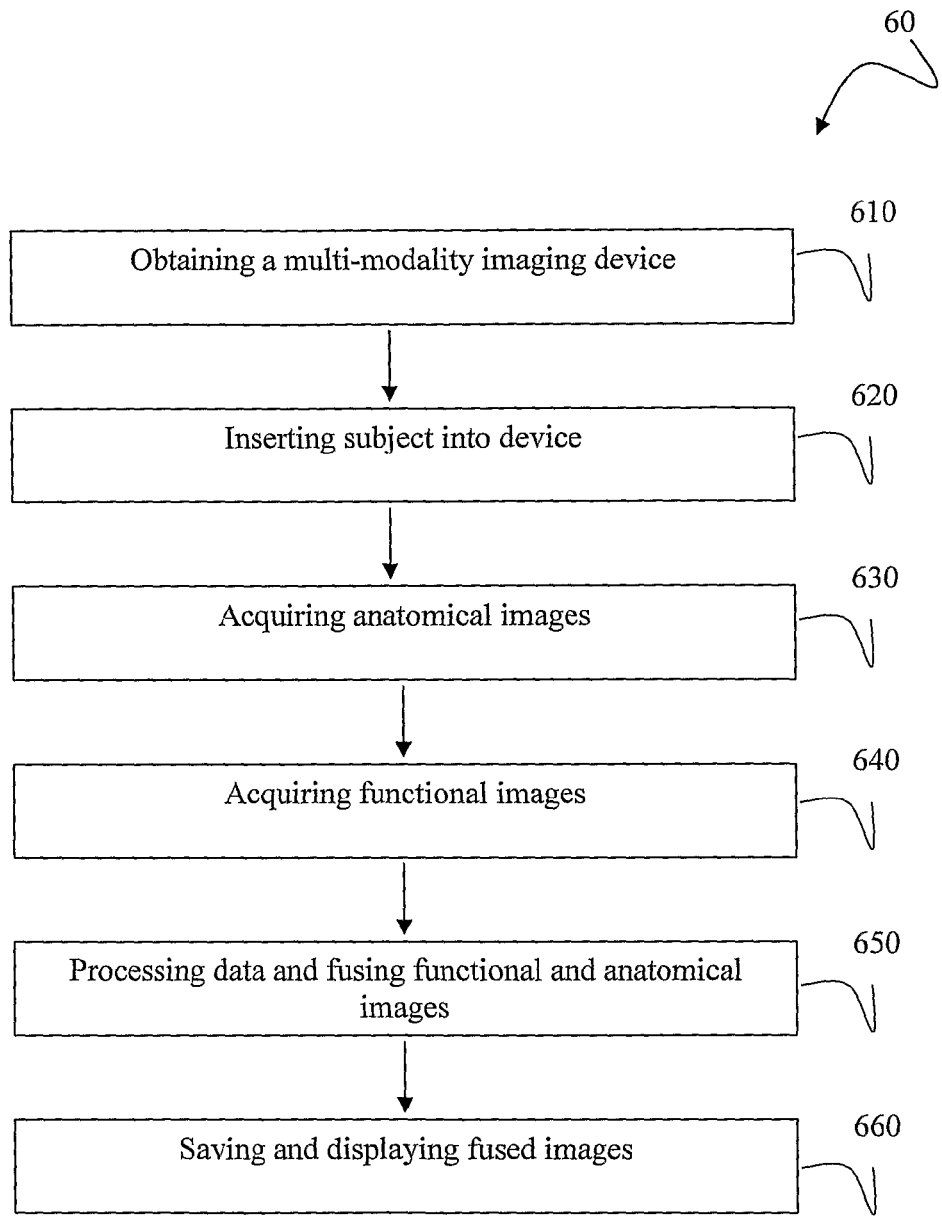
FIG. 6 presents a schematic diagram a method for acquiring integrated (fused) real-time (functional) image of immobilized non-moving subject according an embodiment of the invention herein disclosed.

Reference is now made to FIG. 6, schematically shows a flow chart according to one embodiment of the invention, displaying in a non-limiting manner a method of acquiring in vivo fused images using a multimodality imaging device. The method comprises, inter alia, steps of obtaining a multi-modality spatially fixed coupled imaging device (SFCID) 610, inserting a subject into the device 620, acquiring anatomical images 630, acquiring functional images 640, processing data and fusing functional and anatomical images 650, and saving and displaying fused images 660.

In an illustrative example which is provided below in a non-limiting manner, an immobilized subject of study is inserted into the SFCID as defined in the present invention, both anatomical NMR images are acquired and functional images are acquired. The data is processed and fusing of functional and anatomical images is carried out. The fused images are saved and displayed. The aforesaid functional images, which have been generated by the optical data from the optical sensor array in a preferred embodiment, represent e.g., aspects of the metabolic activity of the tumor. Since the SFCID provides time resolved images, the metabolism of a tumor is monitored over time. This is very important for a wide range of studies, such as cell uptake studies, as well as diagnostic studies of the progress of a malignancy or proliferative cell or tissue disorder. Different drugs can be administered in vivo to a subject undergoing tumor studies or treatment, and the effect on the metabolically active or functionally active part of the tumor can be observed through time. Many malignant tumors have functionally active areas and less active or dead areas. These areas can be monitored accurately in time, in three dimensions.

Since the functional images of the present invention are provided as real time acquisitions, they can be displayed on a single anatomical image which was taken prior to the functional image, in which case the reconstructed fused image will vary with time for each anatomical slice section.

Some anatomical imaging modalities are also capable of producing real-time anatomical images, for example, perfusion images in either CT or MRI, MR-Echo sequences etc. Furthermore, images are sometimes gated, either according to the cardiac rhythm or to the respiratory rhythm. In both cases, both functional and anatomical images can either be acquired simultaneously, or be acquired at different times, and optionally be correlated according to the gating. It is also possible for the functional image to be acquired prior to the acquisition of the anatomical image, or for both modalities to work alternately in the course of one session.

According to one embodiment of the invention, the magnetic resonance imaging (MRI) system includes a detached receiver coil that has the following characteristics: (1) it comprises a single receiver coil independent of the transmit coil; (2) the receiver coil is positionable to allow scanning of a particular volume of choice; (3) the instrument is designed to allow the volume of interest and the receiver coil to be placed at the midpoint of the static magnetic field; (4) the system is adapted not only for acquisition of a 3D MRI image with high sensitivity, positional accuracy, and SNR, but also for acquisition of a 3D image obtained by at least one other spectroscopic method without moving the body being imaged and without the receiver coil blocking the signal being detected by the other method or methods.

According to another embodiment of the invention, the MRI system comprises an RF coil system for imaging one or more regions of a subject. The RF system comprises, inter alia, (a) a coil comprising at least one conductive coil in at least one nonconductive housing; (b) a mechanical translation system adapted for providing linear motion to an attached object and for reproducibly fixing the position of the attached object to within distance X; and (c) attaching means for connecting the housing to the mechanical translation system. The coil system is adapted reversibly to translate the coil to at least one fixed position to an accuracy of about X mm while the subject remains within the magnetic resonance imaging system. X mm (e.g. via a stepper motor); X is any integer number, e.g., X is ranging between about 0.1 mm to about 50 mm; between about 5 mm to about 500 mm, between about 50 mm to 1.5 m etc.

According to another embodiment of the invention, wherein the coil is chosen from the group consisting of (a) a solenoid, (b) a Helmholtz coil, and (c) a surface coil.

According to another embodiment of the invention, the MRI system comprises, inter alia, (a) a magnet for generating a stable magnetic field in a volume, the stable magnetic field defining a magnetic field axis; (b) a plurality of coils for establishing at least one magnetic gradient within the volume; (c) at least one coil for applying pulses of RF radiation to excite nuclear spins of a body located within the volume; and (d) at least one receiver coil as described above, the at least one receiver coil adapted to optimize reception of resonance signals emanating from the body. The magnetic resonance imaging system is adapted to provide at least one magnetic resonance image of at least one predetermined volume within the subject.

According to another embodiment of the invention, least one of the fixed positions is located outside of the volume.

According to another embodiment of the invention, in the MRI system, one of the fixed positions is the point at which the optimized reception occurs at the point along the midpoint of the stable magnetic field along the magnetic field axis.

According to another embodiment of the invention, in the said MRI system, at least one of the fixed positions is located outside of the volume and one of the fixed positions is the point at which the optimized reception occurs at the point along the midpoint of the stable magnetic field along the magnetic field axis According to another embodiment of the invention, the MRI system comprises, inter alia, (a) a second mechanical translation system adapted for providing linear motion to an attached object and for reproducibly fixing the position of the attached object to within about X mm; and (b) attaching means for connecting the bed to the mechanical translation system. It is within the essence of the invention wherein the bed is adapted reversibly to translate relative to the volume independent of the translation of the RF coil.

According to another embodiment of the invention, the MRI system comprises, inter alia, coupling means for connecting the mechanical translation system attached to the bed with the mechanical translation system attached to the RF coil, wherein the motions of the bed and the coil are interdependent.

According to another embodiment of the invention, the MRI system comprises, inter alia, (a) a plurality of detectors disposed about the perimeter of the volume; and (b) means for transmitting a signal from each of the plurality of detectors to a controller located external to the volume. It is within the essence of the invention wherein the magnetic resonance imaging system is adapted for performing at least one type of imaging method in addition to magnetic resonance imaging.

According to another embodiment of the invention, a method for magnetic resonance imaging of a volume of interest in an object to be examined is provided by means of a moveable RF coil system. The method comprises, inter alia, steps of: (a) introducing the object to a predetermined position within a stable magnetic field generated by a magnet; (b) placing a positionable RF receiver coil in proximity to the object such that the position of the RF receiver coil is fixed to within X mm and such that at least part of the volume of interest is located within the volume defined by the coil; (c) exciting nuclear magnetization in the volume of interest by applying RF pulses and magnetic field gradients according to a predetermined imaging protocol; (d) receiving RF imaging signals generated in the RF receiver coil by the excited nuclear magnetization; and (e) reconstructing a magnetic resonance image of the volume of interest from the received magnetic resonance imaging signals and from the position of the RF receiver coil. The method yields an accurate three-dimensional magnetic resonance image of the volume of interest.

According to another embodiment of the invention, the aforesaid method is provided by a means of an RF receiver coil, which is adapted to optimize reception of resonance signals emanating from the volume of interest, and further wherein the step of placing a positionable RF receiver coil in proximity to the object further includes the step of placing the positionable RF receiver at the point along the midpoint of the stable magnetic field along the magnetic field axis.

According to another embodiment of the invention, the aforesaid method is provided by steps of introducing the object to a predetermined position within a stable magnetic field generated by a magnet and of placing a positionable RF receiver coil in proximity to the object are performed by mechanical means adapted to allow independent motion of the body and of the RF receiver coil.

According to another embodiment of the invention, a method for magnetic resonance imaging of a volume of interest in an object to be examined by means of a moveable RF coil system and at least one other imaging technique of the volume of interest is provided. The method comprises, inter alia, steps of: (a) introducing the object to a predetermined position, the predetermined position located within a volume at least part of the interior of which contains stable magnetic field generated by a magnet and about the perimeter of which a plurality of detectors are disposed; (b) placing a positionable RF receiver coil in proximity to the object such that the position of the RF receiver coil is fixed to within X mm and such that at least part of the volume of interest is located within the volume defined by the coil; (c) exciting nuclear magnetization in the volume of interest by applying RF pulses and magnetic field gradients according to a predetermined imaging protocol; (d) receiving RF imaging signals generated in the RF receiver coil by the excited nuclear magnetization; (e) reconstructing a magnetic resonance image of the volume of interest from the received magnetic resonance imaging signals and from the position of the RF receiver coil; and (f) transmitting a signal from each of at least one of the plurality of detectors to a controller located external to the volume, the transmission commencing at a predetermined time relative to the commencement of step (c) and continuing for a predetermined length of time.

According to another embodiment of the invention, the aforesaid method is provided wherein the at least one other imaging technique is chosen from the group consisting of (a) fluorescence spectroscopy; (b) SPECT; (c) PET; (d) any combination of the above.

The invention claimed is:

1. In an MRI system, a spatially fixed coupled imaging device (SFCID) comprising:
   a maneuverable imaging system comprising:
   an imaging platform for accommodating an immobilized subject located within a non-conducting housing;
   an RF coil system encompassing said imaging platform for imaging at least one region of interest of said immobilized subject;
   at least one optical imaging module coupled to said imaging platform and configured to generate at least one optical image of said subject, and
   a coupled imaging system coupled to said maneuverable imaging system and adapted to fuse at least one three-dimensional anatomical image generated by at least one MRI imaging module with said at least one optical image generated by said at least one optical imaging module,
   wherein said fused images provide at least one three-dimensional functional multi-modular real-time image of at least one region of interest of at least one portion of said immobilized subject.

2. The spatially fixed coupled imaging device according to claim 1, wherein said RF coil system comprises:
   an RF transmitting coil encompassing said housing and transmitting RF energy for exciting magnetic nuclei of said subject;
   at least one receiver coil located within said housing and encompassing at least a portion of said subject and a portion of said imaging platform and adapted to receive RF radiation from said at least one region of interest;
   a first displacement system adapted to displace said at least one receiver coil to a fixed location within said housing and said displacement of said at least one receiver coil is selected from the group consisting of a translational displacement with an accuracy of at least 3 mm parallel to a longitudinal axis of said imaging platform, a rotational displacement about said longitudinal axis of said imaging platform and any combination thereof;

a second displacement system adapted for displacing said imaging platform accommodating said immobilized subject and reproducibly fixing a location of said immobilized subject within a range of about 3 mm to about 60 mm from a previous location of said subject and an attaching means for attaching said second displacement system to said housing.

3. The spatially fixed coupled imaging device according to claim 1, wherein said at least one optical imaging module is configured to detect radiation from said at least one region and generate real time functional optical images of said at least one region and said radiation is selected from the group consisting of radiation emitted from said at least one region of interest and radiation reflected by said at least one region of interest.

4. The spatially fixed coupled imaging device according to claim 3, wherein said emitted radiation is selected from the group consisting of detecting bioluminescence, chemiluminescence, fluorescence, near infra-red fluorescence and any combination thereof.

5. The spatially fixed coupled imaging device according to claim 3, wherein said coupled imaging system comprises at least one imaging technique and said at least one imaging technique is selected from the group consisting of fluorescence spectroscopy, SPECT, PET and any combination thereof.

6. The spatially fixed coupled imaging device according to claim 3, wherein said spatially fixed coupled imaging device further comprises at least one of the following: a Two-Dimensional Fourier Transform (2DFT) means and slice selection means for generating said fused image, a Three-Dimensional Fourier Transform (3DFT) means for generating said fused image, a projection reconstruction means for generating said fused image, a point-by-point image generating means for generating said fused image, a line-by-line image generating means for generating said image, a static-field gradient image generating means for generating said fused image, an RF-field gradient image generating means for generating said fused image and any combination thereof.

7. The spatially fixed coupled imaging device according to claim 1, wherein said optical imaging module comprises at least one optical detector array comprising a plurality of optical detectors encompassing said imaging platform in a predetermined manner for providing three dimensional real time optical images of said region of interest.

8. The spatially fixed coupled imaging device according to claim 1, wherein said immobilized subject is selected from the group consisting of at least one human, at least one mammal, at least one biological specimen, at least one biological organ, at least one rodent, at least one bird, at least one reptile, at least one amphibian animal, at least one in-vivo biological tissue, at least one in-vivo organ, at least one ex-vivo biological tissue, at least one ex-vivo organ and any combination thereof.

9. The spatially fixed coupled imaging device according to claim 8, wherein said predetermined manner comprises said plurality of optical detectors circumferentially located on an outer surface of said housing.

10. The spatially fixed coupled imaging device according to claim 1, wherein said at least one MRI imaging module comprises an MRD device.

11. A method for generating images of at least one region of interest of at least one portion of an immobilized subject comprising:
providing a spatially fixed coupled imaging device comprising:
a maneuverable imaging system comprising:
an imaging platform for accommodating said immobilized subject located within a non-conducting housing;
an MRI device comprising an RF coil system encompassing said imaging platform for generating three dimensional anatomical images of said subject; and
at least one optical imaging module coupled to said imaging platform and configured to generate at least one optical image of said subject; and
a coupled imaging system coupled to said maneuverable imaging system and adapted to fuse at least one three-dimensional anatomical image generated by at least one MRI imaging module with said at least one optical image generated by said at least one optical imaging module;
operating said MRI device and said at least one optical imaging module;
generating at least one three-dimensional anatomical image of said at least one region of interest of said subject and at least one optical image of said at least one region of interest of said subject; and
fusing said at least one three-dimensional anatomical images and said at least one optical image and generating at least one three-dimensional functional multimodular fused real-time image of said at least one region of interest of said at least one portion of said immobilized subject.

12. The method according to claim 11, further comprises at least one of the following: generating said fused image from a Two-Dimensional Fourier Transform (2DFT) means and slice selection, generating said fused image from a Three-Dimensional Fourier Transform (3DFT) means, generating said fused image from a projection reconstruction means, generating said fused image from a point-by-point image generating means, generating said fused image from a line-by-line image generating means, generating said fused image from a static-field gradient image generating means, generating said fused image from an RF-field gradient image generating means and any combination thereof.

13. The method according to claim 11, further comprising detecting radiation from said at least one region and generating real time functional optical images of said at least one region and said radiation is selected from the group consisting of radiation emitted from said at least one region of interest and radiation reflected by said at least one region of interest and said emitted radiation is selected from the group consisting of detecting bioluminescence, chemiluminescence, fluorescence, near infra-red fluorescence and any combination thereof.

14. The method according to claim 11, wherein said immobilized subject is selected from the group consisting of at least one human, at least one mammal, at least one biological specimen, at least one biological organ, at least one rodent, at least one bird, at least one reptile, at least one amphibian animal, at least one in-vivo biological tissue, at least one in-vivo organ, at least one ex-vivo biological tissue, at least one ex-vivo organ and any combination thereof.

* * * * *